United States Patent [19]

Lenthe et al.

[11] Patent Number: 4,647,676

[45] Date of Patent: Mar. 3, 1987

[54] PROCESS FOR THE ISOLATION OF 2,2-DIMETHYL-7-HYDROXY-COUMARAN

[75] Inventors: Manfred Lenthe, Odenthal; Udo Allenbach, Cologne; Gerhard Büttner, Pulheim; Karl-Friedrich Christmann, Dormagen, all of Fed. Rep. of Germany

[73] Assignee: Bayer Aktiengesellschaft, Leverkusen, Fed. Rep. of Germany

[21] Appl. No.: 612,962

[22] Filed: May 23, 1984

Related U.S. Application Data

[62] Division of Ser. No. 412,643, Aug. 30, 1982, Pat. No. 4,486,611.

[30] Foreign Application Priority Data

Sep. 16, 1981 [DE] Fed. Rep. of Germany ....... 3136810

[51] Int. Cl.$^4$ ............................................. C07D 307/86
[52] U.S. Cl. .................................... 549/462; 260/705
[58] Field of Search ......................... 549/462; 260/705

[56] References Cited

U.S. PATENT DOCUMENTS

| | | | |
|---|---|---|---|
| 4,297,284 | 10/1981 | Michelet | 549/462 |
| 4,321,204 | 3/1982 | Buttner et al. | 549/462 |
| 4,380,654 | 4/1983 | Franko-Filipassic et al. | 549/462 |

*Primary Examiner*—Richard A. Schwartz
*Assistant Examiner*—Bernard I. Dentz
*Attorney, Agent, or Firm*—Sprung Horn Kramer & Woods

[57] ABSTRACT

A process for the isolation of a dihydroxybenzene-monoether from a reaction mixture containing solvent, ether and unreacted dihydroxybenzene, comprising contacting the reaction mixture with at least one hydrocarbon which is not miscible or only partially miscible with the reaction mixture, the ether selectively entering the hydrocarbon. Advantageously the reaction for the preparation of the monoether is carried out in an alcohol, a ketone, a dipolar aprotic solvent or a polyhydroxyalkyl ether, or a mixture thereof with water, the hydrocarbon used as extracting agent has a boiling point between about 80° and 300° C., and the extraction is carried out in the presence of water whereby there is an increase in the selectivity of the extraction.

3 Claims, No Drawings

PROCESS FOR THE ISOLATION OF 2,2-DIMETHYL-7-HYDROXY-COUMARAN

This is a division of application Ser. No. 412,643, filed Aug. 30, 1982 now U.S. Pat. No. 4,486,611.

The invention relates to an unobvious process for the selective isolation of dihydroxybenzene-monoethers from reaction mixtures obtained in their preparation.

The synthesis of monoethers of dihydroxybenzenes by reacting dihydroxybenzenes with alkyl halides or allyl halides in a solvent in the presence of a base is known (German Published Specification DOS No. 2,845,429, U.S. application Ser. No. 170,443, filed Mar. 15, 1982, now U.S. Pat. No. 4,321,204, and U.S. Pat. No. 3,474,171).

In this synthesis a series of secondary reactions can occur of which in particular further etherification of the monoether in accordance with the following equation

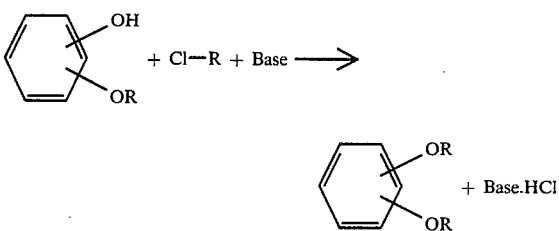

causes considerable lowering of the yield of the monoether desired. This effect increases with increasing activity of the chlorinated hydrocarbon employed.

The known processes try to obtain high yields, for example by appropriate choice of solvents. Thus, for example, ethanol, acetone, dipolar aprotic solvents or polyhydroxyalkyl ethers are known as particularly suitable solvents for the preparation of monoethers of pyrocatechol (see U.S. application Ser. No. 170,443, filed Mar. 15, 1982, now U.S. Pat. No. 4,321,204).

Since the abovementioned formation of the diether is a secondary reaction, it would be advantageous not to react pyrocatechol completely but to interrupt the monoetherification at a conversion which has to be determined exactly. By means of this intervention a high selectivity of the monoether formation could be achieved and, after separating off and returning unreacted dihydroxybenzene, a considerably higher yield of the product desired could also be obtained.

Distillative separations of the mono- and diethers are frequently not possible since the boiling points of the two compounds are too close together. In addition, at the temperatures required for distillation, secondary reactions and hence yield losses may occur.

According to the present invention we provide a process for the isolation of dihydroxybenzene-monoethers from the reaction mixtures obtained in their preparation in which, in addition to solvents and products, unreacted dihydroxybenzene is also present, characterized in that the reaction mixture, if appropriate in the presence of water, is treated with one or more hydrocarbons which are not miscible or not completely miscible with the reaction mixture.

In this process, the dihydroxybenzene-monoether is taken up to a considerable extent by the extracting agent, while the dihydroxybenzene largely remains in the raffinate phase and can be returned into the reaction after suitable working-up steps. The monoether concentrated or isolated in the extract phase can be further processed in the dissolved form given, re-extracted after an appropriate treatment or isolated as a pure substance.

It was surprising that the dihydroxybenzenemonoethers can be separated from the dihydroxybenzenes by a measure, such as liquid/liquid extraction, which is so simple to carry out. The reason this was surprising is that the two compound types are very similar in their chemical and physical properties. They both have free OH groups and similar acid strengths. However, both compound types also have very similar polar properties. The latter in particular are of great importance for a liquid/liquid extraction process. The acentric factor can serve as a measure for these polar properties. The former is a measure of the complexity of a molecule in respect of its geometry (acentricity, sphericity and polarity compare "The Properties of Gases and Liquids", R. C. Reid et al, 3rd edition, McGraw-Hill Book Company). Pyrocatechol thus has an acentric factor of 0.68879.

Isopropoxyphenol has an acentric factor of 0.61865. The two values are relatively close together.

In contrast, an essentially nonpolar compound such as n-octane has a factor of 0.396.

The separation process according to the invention is particularly preferably usable for mixtures of pyrocatechol with pure monoalkyl ethers, such as isopropyl ether, pure monoalkenyl ethers, such as methallyl ether, and pure cyclic alkyl ethers, such as 2,2-dimethyl-7-hydroxycoumaran.

The process according to the invention can be employed particularly advantageously if the monoetherification is carried out in alcohols (such as methanol, or ethanol), in ketones (such as acetone), in dipolar aprotic solvents (such as dimethyl sulphoxide) or in polyhydroxyalkyl ethers (such as glycol monomethyl ether), and their mixtures with water.

Possible hydrocarbons used as extracting agents are open-chain, branched cyclic, saturated and unsaturated hydrocarbons or mixtures of various hydrocarbons; the boiling points of the hydrocarbons being above 50° C. and the hydrocarbons having more than 5 carbon atoms per molecule. The upper limit for the series of extracting agents which can be used is given by the melting point which must be below the operating temperature of the extraction.

Particularly suitable extracting agents are saturated and unsaturated hydrocarbons and mixtures thereof which have boiling points between 80° and 300° C.

The choice of particularly suitable extracting agents for the process according to the invention depends also on the mixtures to be separated.

Thus, to separate pyrocatechol and pyrocatechol monoalkenyl ethers (such as pyrocatechol monomethallyl ether), kerosene (of boling point 170° to 250° C.), n-dodecane, isododecane, heptane, pentamethylheptene and tetraisobutylene are particularly suitable.

To separate pyrocatechol and saturated and cyclic pyrocatechol monomethyl ethers (such as 2,2-dimethyl-7-hydroxycoumaran), 2,2-dimethylpentane, n-dodecane, isododecane, tripropylene and pentamethylheptene are particularly suitable.

In the case of further processing of the extract care must be taken that a physical or chemical separation of the extracted substances and the extracting agent will be possible.

In some cases, the result of the extraction can be further improved by the addition of auxiliary substances. Thus, for example, it has been found that the addition of water increases the selectivity of the extraction.

The process conditions correspond to the procedures for the liquid/liquid extraction described in the general literature (see for example R. H. Perry and C. H. Chilton, Chemical Engineers Handbook, McGraw-Hill, New York).

Further variants are conceivable, for example the extracting agent can already be employed in the reaction to act there as a protective phase. When operating in a continuous manner in a suitable extraction apparatus, the yield of the etherification might thus be considerably increased. To do so, extraction is carried out during the reaction and the extracting agent is separated from the monoether in a parallel-operated column, for example by means of distillation. In this process, the monoether formed is taken up in a protective phase and thus largely removed from the reaction, the result of which is that it cannot react further to give the diether. Yield and selectivity of the reaction are thereby increased.

The process according to the invention can also be used in the selective isolation of high-boiling monoethers, which can be obtained by distillation from the reaction mixtures only with relatively high yield losses.

Thus, for example, 2,2-dimethyl-7-hydroxycoumaran (a cyclic dihydroxybenzene-monoether) obtained by Claisen rearrangement and cyclization from methallyloxyphenol can be extracted from the mixture present after the cyclization, which contains as solvent, for example glycol monomethyl ether and unreacted pyrocatechol.

The present invention is illustrated further by the following examples:

EXAMPLE 1

(a) To examine the extraction efficiency of various hydrocarbons, a batch to prepare methallyloxyphenol by reacting pyrocatechol with methallyl chloride and sodium carbonate as a base in glycol monomethyl ether was carried out as follows:

1,150 g of glycol monomethyl ether, 337 g of technical pyrocatechol (3 mols), 178 g (1.68 mols) of anhydrous sodium carbonate and 5 g of sodium dithionite were initially introduced into a 2.5 liter glass reactor fitted with a small column and a water separator. A slow $N_2$ stream was passed through the well-stirred suspension and the internal temperature raised to about 110° C. 407 g (4.5 mols) of methallyl chloride (MAC) (or when operating with circulation, a corresponding amount of return MAC) were metered in, via a dropping funnel or a metering pump at a uniform rate in the course of 1 hour. Even during the heating-up and during the subsequent reaction, a vigorous $CO_2$ stream commenced. During the entire reaction period of 4.5 hours (inclusive of metering) the water of reaction formed was largely removed. The batch was cooled down to 20° C. and the sodium chloride formed filtered off. The colorless filter residue was washed twice with a little solvent and the amounts of filtrate and the solvent used were combined for washing.

According to a gas chromatogram, the organic phase contained 382 g of pyrocatechol monomethallyl ether (boiling point=58° C./0.1 mm Hg), which corresponded to 78% of theory.

To simulate a lower pyrocatechol conversion, pyrocatechol was added to this solution, so that the mixture employed in the extraction had the following composition:

pyrocatechol—10.6% by weight;
methallyloxyphenol—9.5% by weight;
diether—2.3% by weight;
glycol monomethyl ether—75.2% by weight.

(b) In each case, the solution obtained in Example 1(a) was stirred with the same quantity of the extracting agent. After the two phases (raffinate and extract) had separated, the contents were determined by gas chromatography (internal standard=proportions by weight). The results are listed in the table below.

It must be noted that the hydrocarbons used according to the present invention have a high selectivity for the extraction of the monoether from the polyhydroxybenzene-containing solution.

Thus, for example, pyrocatechol and monoether could be separated virtually completely from one another, for example when using n-dodecane (extraction factor=23.4) in, for example, a multi-stage counter-current extraction.

The effect in respect of the total yield of the monoetherification of, for example, pyrocatechol is an increase in the monoether yield from 78 to about 89%.

TABLE 1

Results of extraction experiments using methallyloxyphenol

| Extracting agent Boiling point/°C. | Extract $PC_E$ | Extract $MOP_E$ | Raffinate $PC_R$ | Raffinate $MOP_R$ | $f_1 = \frac{PC_R}{PC_E}$ | $f_2 = \frac{MOP_R}{MOP_E}$ | $\frac{f_1}{f_2}$ |
|---|---|---|---|---|---|---|---|
| Feed (% by weight): PC:10.68/MOP:9.45/DE:2.29/3-MAPC:0.21 | | | | | | | |
| Cyclohexane 81 | 1.04 | 2.56 | 8.04 | 6.20 | 8 | 2 | 3 |
| n-Heptane 98 | 0.18 | 1.51 | 10.31 | 7.95 | 57 | 5 | 10 |
| 2,2-Dimethylpentane, i-Heptane 81 | 0.17 | 1.36 | 10.13 | 7.98 | 60 | 6 | 10 |
| i-Octane | 0.17 | 1.32 | 9.85 | 8.42 | 58 | 6 | 9 |
| Cleaner's naphtha 100–140 | 0.33 | 1.84 | 9.92 | 7.49 | 30 | 4 | 7 |
| Ligroin 30–110 | 0.31 | 1.68 | 9.66 | 7.56 | 31 | 5 | 7 |
| n-Dodecane 215 | 0.05 | 0.97 | 10.40 | 8.63 | 208 | 9 | 23 |
| i-Dodecane | 0.08 | 0.99 | 10.55 | 8.58 | 132 | 9 | 15 |
| Terapin 155–185 | 0.28 | 1.70 | 9.70 | 7.42 | 35 | 4 | 8 |
| Sangajol 140–200 | 0.26 | 1.65 | 9.68 | 7.50 | 37 | 5 | 8 |
| Kerosene 170–250 | 0.05 | 1.30 | 10.15 | 7.87 | 203 | 6 | 33 |

Feed (% by weight): PC:10.74/MOP:9.21/DE:2.17/3-MAPC:0.12/3-IBPC:0.40

TABLE 1-continued

Results of extraction experiments using methallyloxyphenol

| Extracting agent Boiling point/°C. | Extract $PC_E$ | $MOP_E$ | Raffinate $PC_R$ | $MOP_R$ | $f_1 = \frac{PC_R}{PC_E}$ | $f_2 = \frac{MOP_R}{MOP_E}$ | $\frac{f_1}{f_2}$ |
|---|---|---|---|---|---|---|---|
| Diisobutylene (mixture) | 1.21 | 2.75 | 9.23 | 6.53 | 8 | 2 | 3 |
| Tripropylene (mixture) | 0.42 | 1.93 | 10.00 | 7.28 | 24 | 4 | 6 |
| Tetrapropylene (mixture) | 0.22 | 1.31 | 10.58 | 8.05 | 48 | 6 | 8 |
| 2,4,4,6,6-Pentamethyl-1-heptene | 0.15 | 1.29 | 10.52 | 8.01 | 70 | 6 | 11 |
| Tetraisobutylene (mixture) | 0.10 | 0.92 | 10.85 | 8.43 | 109 | 9 | 12 |

Explanations of the abbreviations
PC pyrocatechol
MOP methallyloxyphenol
DE pyrocatechol dimethallyl ether
3-HAPC 3-methallylpyrocatechol
3-IBPC 3-isobutenylpyrocatechol

EXAMPLE 2

To investigate the process according to the invention further, a mixture of the following composition was used in the extraction:

Contents:
pyrocatechol—0.7% by weight;
2,2-dimethyl-7-hydroxy-coumaran (7-OH)—12.1% by weight;
glycol monomethyl ether—83.0% by weight.

This reaction mixture, obtained from cyclization of 3-methallylpyrocatechol, was in each case mixed with the same amount of extracting agent. After phase separation, the masses of the two phases as well as their contents were determined. The results of these experiments are listed in Table 2.

It is clear that pyrocatechol remained almost completely in the raffinate, but 7—OH was extracted to 26% in a single extraction (n-dodecane).

TABLE 2

Results of extraction of 2,2-dimethyl-7-hydroxycoumaran (7-OH)
PC = pyrocatechol

| Extracting agent | Extract $PC_E$ | 7-$OH_E$ | Raffinate $PC_R$ | 7-$OH_R$ | $f_1 = \frac{PC_R}{PC_E}$ | $f_2 = \frac{7\text{-}OH_R}{7\text{-}OH_E}$ | $\frac{f_1}{f_2}$ |
|---|---|---|---|---|---|---|---|
| Cyclohexane | 0.06 | 2.42 | 0.60 | 8.81 | 10 | 4 | 3 |
| n-Heptane | 0.01 | 0.92 | 0.69 | 11.24 | 69 | 12 | 6 |
| 2,2-Dimethylpentane | — | 0.83 | 0.71 | 11.07 | ∞ | 13 | ∞ |
| i-Octane | 0.01 | 0.31 | 0.72 | 11.07 | 72 | 12 | 6 |
| Cleaner's naphtha | 0.03 | 1.78 | 0.66 | 9.72 | 22 | 6 | 4 |
| Ligroin | 0.01 | 1.31 | 0.70 | 10.88 | 70 | 8 | 8 |
| n-Dodecane | — | 0.48 | 0.72 | 11.79 | ∞ | 25 | ∞ |
| i-Dodecane | — | 0.49 | 0.71 | 11.50 | ∞ | 24 | ∞ |
| Terapin | 0.01 | 1.21 | 0.69 | 10.08 | 69 | 8 | 8 |
| Sangajol | 0.01 | 1.19 | 0.69 | 10.58 | 69 | 9 | 8 |
| Kerosene | 0.23 | 1.44 | 0.63 | 10.87 | 3 | 8 | 0 |
| Diisobutylene (mixture) | 0.10 | 3.12 | 0.70 | 9.97 | 7 | 3 | 2 |
| Tripropylene (mixture) | — | 1.88 | 0.73 | 10.00 | ∞ | 5 | ∞ |
| Tetrapropylene (mixture) | 0.09 | 1.10 | 0.77 | 10.81 | 9 | 10 | 1 |
| 2,3,3,6,6-Pentamethylheptene | — | 1.11 | 0.76 | 10.92 | ∞ | | ∞ |
| Tetraisobutylene (mixture) | | | 0.76 | 11.30 | | 10 | |

It will be appreciated that the instant specification and examples are set forth by way of illustration and not limitation, and that various modifications and changes may be made without departing from the spirit and scope of the present invention.

We claim:

1. A process for the isolation of 2,2-dimethyl-7-hydroxy-coumaran from a reaction mixture containing solvent, cyclic pyrocatechol ether and unreacted pyrocatechol by contacting the reaction mixture with at least one hydrocarbon selected from 2,2-dimethylpentane, n-dodecane, isodecane, tripropylene and pentamethylheptane the ether selectively entering the hydrocarbon.

2. A process according to claim 1, wherein the extraction is carried out in the presence of water whereby there is an increase in the selectivity of the extraction.

3. A process according to claim 1, wherein the cyclic ether is produced by etherifying pyrocatechol with methallyl halide to produce a pyrocatechol monomethallyl ether, and subjecting the monomethallyl ether to rearrangement.

* * * * *